United States Patent [19]

Szymczak

[11] Patent Number: 5,858,343
[45] Date of Patent: Jan. 12, 1999

[54] POST-FOAMING SHAVING GEL INCLUDING POLY(ETHYLENE OXIDE) AND POLYVINYLPYRROLIDONE IN A PREFERRED RANGE OF WEIGHT RATIOS

[75] Inventor: Thomas J. Szymczak, Caledonia, Wis.

[73] Assignee: S. C. Johnson & Son, Inc., Racine, Wis.

[21] Appl. No.: 791,896

[22] Filed: Jan. 31, 1997

[51] Int. Cl.[6] .................................................. A61K 7/15
[52] U.S. Cl. ............................................. 424/73; 424/45
[58] Field of Search .......................................... 424/73, 45

[56] References Cited

U.S. PATENT DOCUMENTS

| | | | |
|---|---|---|---|
| 3,541,581 | 11/1970 | Monson | 252/90 |
| 3,679,102 | 7/1972 | Charle et al. | 222/192 |
| 3,740,421 | 6/1973 | Schmolka | 424/65 |
| 3,852,417 | 12/1974 | McLaughlin | 424/47 |
| 3,923,970 | 12/1975 | Breuer | 424/47 |
| 4,381,293 | 4/1983 | Michel | 424/14 |
| 4,478,853 | 10/1984 | Chaussee | 424/358 |
| 4,495,168 | 1/1985 | Schmolka | 424/45 |
| 4,495,169 | 1/1985 | Schmolka | 424/47 |
| 4,528,111 | 7/1985 | Su | 252/107 |
| 4,534,958 | 8/1985 | Adams et al. | 424/45 |
| 4,548,810 | 10/1985 | Zofchak | 424/59 |
| 4,664,835 | 5/1987 | Grollier et al. | 252/90 |
| 4,917,884 | 4/1990 | Roberts | 424/73 |
| 4,963,352 | 10/1990 | Roberts | 424/73 |
| 4,994,265 | 2/1991 | White | 424/73 |
| 4,999,183 | 3/1991 | Mackles et al. | 424/47 |
| 5,034,220 | 7/1991 | Helioff et al. | 424/73 |
| 5,095,619 | 3/1992 | Davis et al. | 30/41 |
| 5,130,121 | 7/1992 | Kopolow et al. | 424/47 |
| 5,139,770 | 8/1992 | Shih et al. | 424/59 |
| 5,177,113 | 1/1993 | Biss et al. | 514/772.5 |
| 5,248,495 | 9/1993 | Patterson et al. | 424/73 |
| 5,294,438 | 3/1994 | Chang et al. | 424/73 |
| 5,308,643 | 5/1994 | Osipow et al. | 424/73 |
| 5,326,556 | 7/1994 | Barnet et al. | 424/73 |
| 5,334,325 | 8/1994 | Chauss | 252/174.16 |
| 5,340,571 | 8/1994 | Grace | 424/73 |
| 5,342,617 | 8/1994 | Gold | 424/405 |
| 5,345,680 | 9/1994 | Vreeland et al. | 30/41 |
| 5,451,396 | 9/1995 | Villars | 424/73 |
| 5,500,211 | 3/1996 | George et al. | 424/73 |
| 5,560,859 | 10/1996 | Hartmann et al. | 510/135 |
| 5,562,912 | 10/1996 | Burke et al. | 424/401 |

FOREIGN PATENT DOCUMENTS

| | | |
|---|---|---|
| 259 843 | 8/1987 | European Pat. Off. . |
| 259843 | 3/1988 | European Pat. Off. . |
| 503004 | 9/1992 | European Pat. Off. . |
| 550281 | 7/1993 | European Pat. Off. . |
| 1444334 | 7/1976 | United Kingdom . |

OTHER PUBLICATIONS

Union Carbide Corporation, "Polyox® Water–Soluble Resins", 1988.
International Specialty Products, "Specialty Products for Personal Care: Reference Guide", 1996

*Primary Examiner*—Neil S. Levy

[57] ABSTRACT

A composition for use as a post-foaming shaving gel, for example, comprising about 3% to about 20% by weight of the composition of a surfactant system, about 0.05% to about 10% by weight of the composition of poly(ethylene oxide) and polyvinylpyrrolidone, in a combined amount, wherein the poly(ethylene oxide) and the polyvinylpyrrolidone are present in a weight ratio of about 1:10 to about 10:1, and about 0.1% to about 10% by weight of the composition of a post-foaming agent.

38 Claims, No Drawings

POST-FOAMING SHAVING GEL INCLUDING POLY(ETHYLENE OXIDE) AND POLYVINYLPYRROLIDONE IN A PREFERRED RANGE OF WEIGHT RATIOS

BACKGROUND OF THE INVENTION

1. Field of the Invention

This invention relates to the field of post-foaming compositions, more particularly to post-foaming shaving gels, and still more particularly to a post-foaming shaving gel including (a) a surfactant system, (b) the polymers poly(ethylene oxide) and polyvinylpyrrolidone, preferably in a weight ratio falling within a specified range, and (c) a post-foaming agent.

2. Description of the Related Art

Post-foaming shaving gels, also known as "self-foaming" or just "foaming" shaving gels, have become popular because of their unique characteristics: in use, the product is dispensed from a container in a gel form substantially free from foam, and is transformed into a foam when rubbed onto the skin. (In this respect, post-foaming shaving gels differ from "shaving creams", which are dispensed as foam.) To effect the transformation from gel to foam, a post-foaming agent comprising a hydrocarbon propellant is typically provided in the post-foaming shaving gel. The post-foaming agent volatilizes when the post-foaming shaving gel is rubbed onto the skin, thereby changing the post-foaming shaving gel into a foamy lather.

In addition to the post-foaming agent, other ingredients of known post-foaming shaving gels have included, for example, surfactants for cleaning (including soaps and synthetic detergents), gellants (also known as gelling aids) or thickeners, agents for adjusting lubricity, water, humectants, emollients, fragrances, and colorants.

As for gellants, thickeners, and agents for adding lubricity, in particular, a variety of ingredients have been mentioned in the related art. For example, U.S. Pat. No. 5,451,396 (commonly assigned to the assignee of the present application) to Villars lists as preferred gelling aids "water-soluble hydroxyalkyl cellulose or naturally derived gums such as xanthan, various synthesized polymers such as polyvinyl pyrrolidone, as well as chemical or enzymatically modified derivatives of these materials." U.S. Pat. No. 5,326,556 to Barnet, et al. refers to polyethylene oxide and hydroxyethyl cellulose as preferred water-soluble polymers. U.S. Pat. No. 5,560,859 to Hartmann, et al. discusses use of poly(ethylene oxide) as a gel stabilizer.

Several of the aforementioned compounds are found in a series of conventional shaving gels (referred to as the 14614D series) manufactured by S. C. Johnson & Son, Inc., the assignee of the present application. Each of those gels includes, among other ingredients, (a) poly(ethylene oxide) (POLYOX® WSR 301), (b) hydroxyethyl cellulose, (c) a soap with stearic acid, palmitic acid, and triethanolamine, and (d) a post-foaming agent with either (i) isopentane and isobutane or (ii) n-pentane and isobutane. These gels, hereinafter, collectively will be referred to as the "conventional S. C. Johnson shaving gel."

However, conventional post-foaming shaving gels, such as the conventional S. C. Johnson shaving gel, leave room for improvement in a number of respects. Consider, for example, the conventional S. C. Johnson shaving gel. That shaving gel is an excellent shaving composition; nonetheless, a number of areas for improvement were noticed, both in manufacturing and in use. In the manufacturing process, the ingredients which comprise the shaving gel were mixed together, and the resulting, substantially liquid mixture was filled into an open, unpressurized container (such as, for example, an aerosol can), which was then pressurized and capped. To convert the substantially liquid mixture to gel form, it was necessary to let the container rest at about room temperature for about two weeks. In some cases, it was necessary to heat the container to about 130° F. for about two to three hours to provide energy sufficient to effect the conversion to gel form. Not only was the conversion from liquid to gel form difficult, but another disadvantage was present in the manufacturing process: when the substantially liquid mixture was dispensed into the open, unpressurized container, it tended to foam rapidly if post-foaming agents having a high vapor pressure were used, or if large amounts of high or low vapor pressure post-foaming agents were used. Of course, such foaming was unacceptable because the product was intended to be a substantially foam-free gel. As a result, it was necessary to use post-foaming agents having a lower vapor pressure, or to reduce the total amount of post-foaming agents, so as to obviate the foaming problem. However, both of these solutions were disadvantageous because, when the resulting shaving gel was used, it produced a foam which was denser, heavier, and less commercially desirable than that produced by shaving gels incorporating higher-vapor pressure post-foaming agents or a greater total amount of post-foaming agents.

In addition to these manufacturing problems, a number of disadvantages arose with the conventional S. C. Johnson post-foaming shaving gel when used. For example, the characteristics of the post-foaming shaving gel were such that it was not as easy as desired to rinse the foam produced by the post-foaming shaving gel from the skin. In addition, although the post-foaming shaving gel remained in a substantially foam-free form for a number of minutes upon being dispensed, it was commercially desirable to increase this amount of time.

I believe that other commercially available post-foaming shaving gels have the same or similar disadvantages, in manufacture or use.

Accordingly, a need has arisen to overcome drawbacks associated with conventional post-foaming shaving gels, such as those discussed above, and to provide a composition, such as a post-foaming shaving gel, for example, having improved properties.

SUMMARY OF THE INVENTION

In view of the foregoing, one object of this invention is to provide a composition, such as a post-foaming shaving gel which reduces or eliminates the problem of foaming during the filling step of manufacturing.

Another object of this invention is to provide a composition, such as a post-foaming shaving gel which reduces the amount of time, heat, or energy necessary to effect a conversion from liquid to gel form during manufacturing.

Still another object of this invention is to provide a composition, such as a post-foaming shaving gel which permits use of higher vapor pressure post-foaming agents, or which permits use of a greater total amount of post-foaming agents, in comparison with conventional post-foaming shaving gels, thereby generating a more voluminous, more commercially-acceptable foam when the gel is applied to the skin.

A further object of this invention is to provide a composition, such as a post-foaming shaving gel which, when dispensed under static conditions, remains in a substantially gel-like and foam-free form for a longer period of time than conventional post-foaming shaving gels, especially when dispensed under environmental conditions of about 14 to about 50 psia and about 32° F. to about 150° F.

Another object of this invention is to provide a composition, such as a post-foaming shaving gel which is easier to rinse from the skin than conventional post-foaming shaving gels.

Yet another object of this invention is to provide methods for making a composition, such as a post-foaming shaving gel having the desired properties of this invention.

A still further object of this invention is to provide a composition having the desired properties of this invention, and methods for making the same.

In view of the foregoing objects, in one aspect, this invention relates to a composition, such as a post-foaming shaving gel composition comprising about 3% to about 20% by weight of the composition of a surfactant system, about 0.05% to about 10% by weight of the composition of poly(ethylene oxide) and polyvinylpyrrolidone, in a combined amount, wherein the poly(ethylene oxide) and the polyvinylpyrrolidone are present in a weight ratio of about 1:10 to about 10:1, and about 0.1% to about 10% by weight of said composition of a post-foaming agent.

In another aspect, this invention relates to a composition comprising about 3% to about 20% by weight of the composition of a surfactant system, about 0.05% to about 10% by weight of the composition of poly(ethylene oxide) and polyvinylpyrrolidone, in a combined amount, wherein the poly(ethylene oxide) and the polyvinylpyrrolidone are present in a weight ratio of about 1:10 to about 10:1, and about 0.1% to about 10% by weight of the composition of a post-foaming agent.

In yet another aspect, this invention relates to a gel comprising about 3% to about 20% by weight of the gel of a soap, about 0.05% to about 10% by weight of the gel of poly(ethylene oxide) and polyvinyl-pyrrolidone, in a combined amount, wherein the poly(ethylene oxide) and the polyvinylpyrrolidone are present in a weight ratio of about 1:10 to about 10:1, and about 0.1% to about 10% by weight of the gel of a post-foaming agent comprising a hydrocarbon propellant.

In still another aspect, this invention relates to a composition in the form of a post-foaming gel, comprising about 3% to about 20% by weight of the composition of a water-soluble salt of a higher fatty acid, about 0.05% to about 10% by weight of the composition of (a) poly (ethylene oxide) having about 60,000 to about 120,000 linked ethylene oxide monomers and (b) polyvinylpyrrolidone, in a combined amount, wherein the poly(ethylene oxide) and the polyvinylpyrrolidone are present in a weight ratio of about 1:1 to about 1:10, and about 0.1% to about 10% by weight of the composition of a post-foaming agent comprising a hydrocarbon propellant selected from the group consisting of propane, n-pentane, isopentane, neopentane, n-butane, isobutane, and mixtures thereof, wherein the composition has a pH of about 4 to about 10.

The above-noted and other objects, advantages, and features of this invention will become more apparent from the following description of the preferred embodiments.

DETAILED DESCRIPTION OF THE PREFERRED EMBODIMENTS AND BEST MODE FOR CARRYING OUT THE INVENTION

The preferred embodiments and the best mode for carrying out the invention will now be described.

In a preferred embodiment, this invention is a composition, such as a post-foaming shaving gel, comprising (a) a surfactant system, (b) the two polymers poly (ethylene oxide) and polyvinylpyrrolidone, within a preferred range of weight ratios, and (c) a post-foaming agent. For ease of discussion, the composition of this invention will be referred to as a "post-foaming shaving gel." However, one having ordinary skill in the art would recognize that the composition of this invention is also useful, for example, as a laundry prespotter, a drain freshener, a hard surface cleaner, or a personal cleaner such as a body wash or a hand soap.

The post-foaming shaving gel of this invention may also comprise a variety of optional ingredients, including water, humectants, emollients, colorants, and fragrances. Preferably, the pH of the post-foaming shaving gel of this invention is about 4 to about 10, more preferably about 7 to about 10, and most preferably about 8 to about 9.

In the discussion below, all percentages are by weight of the total post-foaming shaving gel composition, unless specified otherwise.

The Surfactant System

The surfactant system of the post-foaming shaving gel of my invention preferably comprises a soap, or a synthetic detergent, or one or more of either or both. The surfactant system preferably is present in an amount of about 3% to about 20% by weight of the total post-foaming shaving gel composition, and more preferably in an amount of about 16 to about 18%, and most preferably in an amount of about 17%. These ranges are preferable whether the surfactant system includes only soaps, or only synthetic detergents, or both.

The soap of the surfactant system preferably comprises a water-soluble salt of a fatty acid, most preferably a higher fatty acid. The soap of the surfactant system may be preformed. Alternatively, the soap may be formed or prepared in any conventional manner. For example, the soap may be prepared in situ by reacting a basic material such as, for example, triethanolamine (also known as "TEA"), sodium hydroxide, or potassium hydroxide with a higher fatty acid such as, for is example, stearic, palmitic, myristic, oleic, or coconut oil fatty acid, or mixtures of these higher fatty acids. The triethanolamine soaps of stearic and palmitic acids are preferred ingredients of the surfactant system, and either one or more, and preferably both of these two soaps may be used. Preferably an excess of the basic material, such as triethanolamine, for example, is added to completely neutralize the fatty acid and to adjust the pH to the desired range.

As mentioned above, the surfactant system may comprise a synthetic detergent. I prefer that the synthetic detergent be non-ionic in character and soluble in the aqueous components of the composition. If the surfactant system comprises soap and synthetic detergent, it is preferable that the synthetic detergent be present in an amount of about 0.1% to about 8% by weight of the shaving gel composition, with the soap and synthetic detergent combined preferably totalling about 3% to about 20% by weight of the composition. Preferred synthetic detergents include water-soluble polyoxyethylene ethers of alkyl-substituted phenols, and water-soluble polyethoxylated derivatives of fatty alcohols. A particularly preferred synthetic detergent is Oleth-20, which is defined in the *CTFA Cosmetic Ingredient Handbook,* First Edition (1988), published by the Cosmetic, Toiletry and Fragrance Association, Inc., and incorporated herein in its entirety by reference.

Another class of preferred synthetic detergents are the water-soluble N-acyl sarcosinate salts. The N-acyl sarcosine of the N-acyl sarcosinate salt preferably is selected from those having an acyl moiety of 10 to 20 carbon atoms, and more preferably 12 to 18. The N-acyl sarcosine preferably is neutralized with a base (preferably an organic amine base, such as, e.g., triethanolamine) to produce the water-soluble salt. Preferred N-acyl sarcosines include, for example, stearoyl sarcosine, myristoyl sarcosine, oleoyl sarcosine, lauroyl sarcosine, cocoyl sarcosine, and mixtures of these sarcosines. The N-acyl sarcosine salt may be provided preformed, or may be formed in situ by neutralizing with a base as described above. The pH of the shaving gel composition preferably may be set by regulating the amount of base in this neutralization reaction.

The foregoing preferred synthetic detergents are given by way of example and not by way of limitation. Any other synthetic detergents may be employed in the surfactant system, although it is less preferable to include those which are known in the art to have an adverse effect on gel formation, such as, for example, sodium lauryl sulfate and TEA lauryl sulfate.

Overall, the surfactant system preferably comprises, and more preferably consists essentially of, a mixture of soaps of palmitic and stearic acids, preferably prepared by combining triethanolamine, palmitic acid, and stearic acid to yield triethanolamine salts of the two acids. (Alternatively, the stearic acid may be omitted to yield a soap of palmitic acid.) A weight ratio of palmitic acid to stearic acid of 1:3 to 3:1 is preferred, with a ratio of about 3:1 being even more preferred. Preferably, the soaps of the surfactant system are triethanolamine soaps. Most preferably, the palmitic acid used is that designated as "palmitic acid 93.5%", and sold by Acme-Hardesty, while the stearic acid is that sold under the trademark "Emersol 132" by Emery Industries.

Poly(ethylene oxide) and Polyvinylpyrrolidone

Poly(ethylene oxide), also referred to in the art as "polyoxyethylene", "poly(oxyethylene)", "polyethylene glycol", and "PEG", is a linear homopolymer of ethylene oxide monomers that conforms generally to the formula $H(OCH_2CH_2)_nOH$, and is non-ionic and water-soluble. Preferably, n has an average value of about 15,000 to about 120,000, more preferably about 60,000 to about 120,000, and most preferably about 90,000. "PEG-90M" is the art-recognized name for the case where the average value of n is 90,000, as defined in the CTFA Cosmetic Ingredient Handbook, First Edition (1988), which is incorporated herein in its entirety by reference. The preferred grade of PEG-90M for this invention is that which is sold under the name "POLYOX® WSR 301" by Union Carbide Corporation, and which has an approximate molecular weight of about four million.

Polyvinylpyrrolidone is a linear homopolymer of 1-vinyl-2-pyrrolidone monomers, and is water-soluble. Polyvinylpyrrolidone is also known as "PVP", and a definition thereof is set forth in the CTFA Cosmetic Ingredient Handbook, First Edition (1988), which is incorporated herein in its entirety by reference. Preferably, the polyvinylpyrrolidone used in this invention has an average molecular weight (Mv) in Daltons of about 630,000. Most preferably, the polyvinylpyrrolidone used in this invention is that which is sold in powder form under the name "PVP K-90" by International Specialty Products.

I prefer that the ratio by weight of poly(ethylene oxide) to polyvinylpyrrolidone be within the range of about 1:10 to about 10:1, more preferably within the range of 1:1 to 1:10, and optimally about 9:47 (i.e., about 1:5). This is because I found that, if too much poly(ethylene oxide) was added, the gel would be undesirably elastic, while if too much polyvinylpyrrolidone was added, the gel would be undesirably stiff.

The poly(ethylene oxide) and polyvinylpyrrolidone preferably are present in an amount of about 0.05% to about 10%, totalled together, by weight of the total post-foaming shaving gel composition. Most preferably, the poly(ethylene oxide) and polyvinylpyrrolidone are present in an amount of about 0.56% (i.e., about 0.6%).

Comparative tests have shown that post-foaming shaving gels according to this invention are remarkably superior to conventional post-foaming shaving gels.

Furthermore, the post-foaming shaving gels according to this invention have made it possible to eliminate a number of ingredients used in the conventional S. C. Johnson post-foaming shaving gel, thereby simplifying and reducing the cost of manufacturing. For example, it was possible to eliminate hydroxyethyl cellulose, and it is thought that compositions according to this invention may be prepared free from such gelling aids such as alkyl glycols, polyacrylic acids, alkyl modified cellulose polymers, guar gums, xanthan gums, and mixtures thereof. Other ingredients that successfully were eliminated included lauryl alcohol and palmitamine oxide.

Post-foaming Agent

The post-foaming agent preferably comprises at least one hydrocarbon propellant selected from the group consisting of propane, n-pentane, isopentane, neopentane, n-butane, isobutane, and mixtures thereof. More preferably, the post-foaming agent comprises, and most preferably consists of, a mixture of isobutane and isopentane. Preferably, the weight ratio of isobutane:isopentane is about 0.70:2.25 (i.e., about 1:3). The post-foaming agent preferably is present in an amount of about 0.1 to about 10% by weight of the total post-foaming shaving gel composition, and more preferably about 3%. Most preferably, the isobutane used is A-31 propellant, sold under the names "AEROPRES 31" (Aeropres Corp.), "AERON 31" (Diversified Chemicals), "A-31" (Phillips Petroleum), "MAIP-31 Propellant" (Demert), or "A-31" (Technical Propellants)

Water

Water serves as a solvent for the surfactant system, and also aids in softening the hair which is to be removed from the skin during shaving, when the composition of this invention is formulated as a post-foaming shaving gel. Water is preferably present in an amount of at least about 60% by total weight of the post-foaming shaving gel composition, and most preferably in an amount of about 75% by total weight. The addition of too much water might soften the gel undesirably, while the use of too little water might make the gel too thick to manufacture easily. Preferably, deionized water is used, as the use of ionized water might have an adverse effect upon gel formation.

Optional Ingredients

The post-foaming shaving gel according to this invention may include one or more optional ingredients or adjuvants, including, for example, emollients, humectants, colorants, and fragrances, which will be discussed in turn below. A variety of such additional optional ingredients or adjuvants may be added, as long as they do not materially change the fundamental character of the post-foaming shaving gel composition.

a. Emollients

Emollients provide lipids to replenish those lost in shaving, for example, and also may soften the hair to be removed by the razor during shaving so as to make it easier to cut. Secondarily, some emollients also have some effect on gel strength. Examples of preferred emollients include glycol esters selected from the group consisting of propylene glycol monoisostearate, propylene glycol dipelargonate, propylene glycol oleate, propylene glycol myristate, and mixtures thereof, with propylene glycol monoisostearate being preferred.

Examples of especially preferred emollients include a distilled monoglyceride of sunflower oil which is sold under the trademark "Myverol 18-92" by Eastman Chemical Products, and lanolin alcohol (preferably "Super Hartolan" lanolin alcohol, sold by Croda).

b. Humectants

Humectants optionally may be included, and serve to retain water, to prevent the gel from drying out, and to prevent the nozzle of the dispenser, in which the post-foaming shaving gel may be stored, from drying up and clogging. Examples of preferred humectants include polyhydric alcohols selected from the group consisting of ethylene glycol, propylene glycol, butylene glycol, glycerin, and sorbitol, with sorbitol being most preferred. Preferably, the sorbitol used in this invention is that which is referred to in the art as "sorbitol, 70% USP" (USP refers to the U.S. Pharmacopeia reference handbook, which is incorporated herein in its entirety by reference), most preferably that which is sold by ADM Food Additives, Merck (under the name "Sorbo"), Roquette, or Pfizer Chemicals.

The glycerin used in this invention is preferably "glycerin, USP, 99.5%", most preferably that which is sold by Dow Chemical, Inc., Emery Industries, Inc. (under the name "Superol 99.5%"), and Procter & Gamble. Another preferred humectant is "DL-panthenol", which is sold by Hoffman-Laroche. Yet another preferred humectant is PEG/PPG 17/6 copolymer (17 moles ethylene oxide/6 moles propylene oxide), preferably that sold by PPG/Mazer Chemicals or Union Carbide, under the names "Macol 450" and "Ucon 75-H-450". Still another preferred humectant is phytantriol, preferably that sold by Roche.

c. Colorants

Colorants may also be added, optionally. Preferably, the colorants are those which have been approved for use in shaving gels, such as, for example, D&C dyes and FD&C dyes. Preferred examples of colorants include FD&C Blue #1, D&C Yellow #10, D&C Green #8, D&C Red #33, and FD&C Red #40, preferably those sold by H. Kohnstamm & Co., Warner Jenkinson, or Hilton Davis.

d. Fragrances

Fragrances optionally may be included for cosmetic effect, and preferably should be compatible with water-soluble soaps and detergents. Any known cosmetically acceptable fragrance may be employed. Fragrances preferably are present in a total amount less than or equal to 1% by total weight of the post-foaming shaving gel composition, and more preferably less than or equal to 0.5%.

e. Other Ingredients

As noted above, other ingredients or adjuvants optionally may be included in the post-foaming shaving gel according to this invention. Examples thereof include anti-oxidants such as BHT (preferably, "Sustane BHT" sold by Quest), vitamin E, aloe vera powder (preferably "Co Vera Dry" sold by Costec, Inc., or that which is sold by Tri-K), allantoin (preferably that sold by Sutton Labs), or any other materials which provide desired properties.

EXAMPLES

The following examples set forth in TABLES 1, 2, 3, amd 4, namely EXAMPLES 1 through 14, are illustrative of compositions in accordance with this invention. All amounts are given in percent by weight of the composition unless specified otherwise.

TABLE 1

| MATERIAL | EXAMPLE 1 | EXAMPLE 2 | EXAMPLE 3 |
|---|---|---|---|
| DEIONIZED WATER | 74.533070 | 74.576743 | 74.389630 |
| PALMITIC ACID, 93.5% | 8.006625 | 8.006625 | 8.006625 |
| TRIETHANOLAMINE, 99%, LFG | 7.036125 | 7.036125 | 7.036125 |
| STEARIC ACID | 2.668875 | 2.668875 | 2.668875 |
| SORBITOL, 70% | 1.941000 | 1.941000 | 1.955558 |
| MYVEROL 18-92 | 1.941000 | 1.941000 | 1.953617 |
| POLYOX WSR 301 | 0.087345 | 0.087345 | 0.087345 |
| PVP K-90 | 0.446430 | 0.446430 | 0.446430 |
| FRAGRANCE 1 | 0.388200 | 0.329970 | 0.388200 |
| LANOLIN ALCOHOL | | | |
| GLYCERIN, USP, 99.5% | | | 0.097050 |
| FRAGRANCE 2 | | | |
| DL PANTHENOL 50% LIQUID | | | |
| PEG/PPG 17/6 COPOLYMER | | | |
| VITAMIN E ACETATE, USP | | | |
| FRAGRANCE 3 | | | |
| FRAGRANCE 4 | | | |
| PHYTANTRIOL | | | |
| FRAGRANCE 5 | | | |
| FRAGRANCE 6 | | | |
| BHT | | | |
| ALLANTOIN | | | |
| ALOE VERA POWDER | | 0.014558 | 0.019410 |
| FD&C BLUE #1 | 0.001058 | 0.001058 | 0.000862 |
| D&C YELLOW #10 | 0.000272 | 0.000272 | 0.000274 |
| D&C GREEN #8 | | | |
| ISOBUTANE | 0.700000 | 0.700000 | 0.700000 |
| ISOPENTANE | 2.250000 | 2.250000 | 2.250000 |
| TOTAL | 100.00 | 100.00 | 100.00 |

TABLE 2

| MATERIAL | EXAMPLE 4 | EXAMPLE 5 | EXAMPLE 6 |
|---|---|---|---|
| DEIONIZED WATER | 74.505895 | 74.726911 | 74.533066 |
| PALMITIC ACID, 93.5% | 8.006625 | 8.006625 | 8.006625 |
| TRIETHANOLAMINE, 99%, LFG | 7.036125 | 7.036125 | 7.036125 |
| STEARIC ACID | 2.668875 | 2.668875 | 2.668875 |
| SORBITOL, 70% | 1.955558 | 1.649850 | 1.941000 |
| MYVEROL 18-92 | 1.953617 | 1.941000 | 1.941000 |
| POLYOX WSR 301 | 0.087345 | 0.087345 | 0.087345 |
| PVP K-90 | 0.446430 | 0.446430 | 0.446430 |
| FRAGRANCE 1 | 0.388200 | 0.388200 | |
| LANOLIN ALCOHOL | | 0.097050 | |
| GLYCERIN, USP, 99.5% | | | |
| FRAGRANCE 2 | | | 0.388200 |
| DL PANTHENOL 50% LIQUID | | | |
| PEG/PPG 17/6 COPOLYMER | | | |
| VITAMIN E ACETATE, USP | | | |
| FRAGRANCE 3 | | | |
| FRAGRANCE 4 | | | |

TABLE 2-continued

| MATERIAL | EXAMPLE 4 | EXAMPLE 5 | EXAMPLE 6 |
|---|---|---|---|
| PHYTANTRIOL | | | |
| FRAGRANCE 5 | | | |
| FRAGRANCE 6 | | | |
| BHT | | | |
| ALLANTOIN | | | |
| ALOE VERA POWDER | | | |
| FD&C BLUE #1 | 0.001058 | 0.000397 | 0.000340 |
| D&C YELLOW #10 | 0.000272 | | 0.000995 |
| D&C GREEN #8 | | 0.001192 | |
| ISOBUTANE | 0.700000 | 0.700000 | 0.700000 |
| ISOPENTANE | 2.250000 | 2.250000 | 2.250000 |
| TOTAL | 100.00 | 100.00 | 100.00 |

TABLE 3

| MATERIAL | EXAMPLE 7 | EXAMPLE 8 | EXAMPLE 9 |
|---|---|---|---|
| DEIONIZED WATER | 74.614288 | 74.747910 | 73.203485 |
| PALMITIC ACID, 93.5% | 8.006625 | 8.006625 | 8.006625 |
| TRIETHANOLAMINE, 99%, | 7.036125 | 7.036125 | 7.036125 |
| LFG | | | |
| STEARIC ACID | 2.668875 | 2.668875 | 2.668875 |
| SORBITOL, 70% | 1.941000 | 1.941000 | 1.941000 |
| MYVEROL 18-92 | 1.941000 | 1.941000 | 1.941000 |
| POLYOX WSR 301 | 0.087345 | 0.087345 | 0.087345 |
| PVP K-90 | 0.446430 | 0.446430 | 0.446430 |
| FRAGRANCE 1 | | | 0.388200 |
| LANOLIN ALCOHOL | | | |
| GLYCERIN, USP, 99.5% | | | 0.320265 |
| FRAGRANCE 2 | | | |
| DL PANTHENOL 50% LIQUID | | | 0.582300 |
| PEG/PPG 17/6 COPOLYMER | | | 0.320265 |
| VITAMIN E ACETATE, USP | | 0.097050 | 0.097050 |
| FRAGRANCE 3 | 0.159162 | | |
| FRAGRANCE 4 | 0.098991 | | |
| PHYTANTRIOL | | | 0.009705 |
| FRAGRANCE 5 | | 0.048525 | |
| FRAGRANCE 6 | 0.039791 | | |
| BHT | | 0.029115 | |
| ALLANTOIN | 0.009705 | | |
| ALOE VERA POWDER | | | |
| FD&C BLUE #1 | 0.000664 | | 0.001058 |
| D&C YELLOW #10 | | | 0.000272 |
| D&C GREEN #8 | | | |
| ISOBUTANE | 0.700000 | 0.700000 | 0.700000 |
| ISOPENTANE | 2.250000 | 2.250000 | 2.250000 |
| TOTAL | 100.00 | 100.00 | 100.00 |

TABLE 4

| MATERIAL | EXAMPLE 10 | EXAMPLE 11 | EXAMPLE 12 | EXAMPLE 13 | EXAMPLE 14 |
|---|---|---|---|---|---|
| DEIONIZED WATER | 73.333739 | 73.662025 | 73.951615 | 72.179372 | 76.135835 |
| PALMITIC ACID, 93.5% | 7.971150 | 7.971150 | 7.971150 | 8.695800 | 5.951792 |
| TRIETHANOLAMINE, 99%, LFG | 7.478388 | 7.478388 | 7.478388 | 8.101587 | 6.879344 |
| STEARIC ACID | 2.657050 | 2.657050 | 2.657050 | 2.898600 | 3.710208 |
| SORBITOL, 70% | 1.903414 | 1.903414 | 1.903414 | 1.903414 | 0.966200 |
| MYVEROL 18–92 | 1.777808 | 1.932400 | 1.777808 | 1.777808 | 1.207750 |
| POLYOX WSR 301 | 0.086958 | 0.086958 | 0.086958 | 0.086958 | 0.086958 |
| PVP K-90 | 0.444452 | 0.444452 | 0.444452 | 0.444452 | 0.444452 |
| FRAGRANCE 7 | 0.386480 | | 0.241550 | | |
| LANOLIN ALCOHOL | 0.483100 | | | | |
| FRAGRANCE 8 | | 0.386480 | | | |
| STANDAMID KD | | | | | 0.241550 |
| DODECANOL | | | | | 0.483100 |
| VITAMIN E ACETATE, USP | 0.096620 | 0.096620 | 0.096620 | 0.096620 | 0.096620 |
| FRAGRANCE 9 | | | | 0.386480 | |
| MINERAL OIL | | | | 0.048310 | |
| FRAGRANCE 10 | | | | | 0.386480 |
| PEG-150 DISTEARATE | | | | | 0.019324 |
| D&C GREEN | | | | | 0.000541 |
| BHT | | | | | 0.009662 |
| D&C YELLOW #10 | | | 0.000480 | 0.000029 | |
| ALOE VERA POWDER | | | 0.009662 | | |
| D&C RED #33 | 0.000242 | 0.000966 | | 0.000128 | |
| FD&C RED #40 | 0.000599 | | | | |
| FD&C BLUE #1 | | 0.000097 | 0.000853 | 0.000443 | 0.000184 |
| ISOBUTANE | 0.880000 | 0.880000 | 0.880000 | 0.880000 | 0.880000 |
| ISOPENTANE | 2.500000 | 2.500000 | 2.500000 | 2.500000 | 2.500000 |
| TOTAL | 100.00000 | 100.00000 | 100.00000 | 100.00000 | 100.00000 |

Manufacturing Process

The foregoing post-foaming shaving gel examples (EXAMPLES 1 through 14) preferably are prepared by the following method. First, the water is placed in a closed container. Next, the colorants are mixed into the water, followed by the polyvinylpyrrolidone. The mixture is heated to about 180° F. The poly(ethylene oxide) is dispersed in sorbitol, and the resulting dispersion is added to the mixture and blended. Next, the surfactant system is added as follows. First, an excess of triethanolamine is added, followed by the fatty acids themselves, e.g., stearic acid and palmitic acid.

The reason that an excess of triethanolamine is added is to ensure that all of the fatty acids are neutralized. Preferably, the amount of triethanolamine is adjusted to yield a final pH for the post-foaming shaving gel of about 4 to about 10, more preferably about 7 to about 10, and most preferably about 8 to about 9. Next, the emollient "Myverol 18-92" is mixed in. The mixing continues for about one hour (for approximately a 40,000 lb batch). Thereafter, the mixture is left to cool to about 75° F. As for the remaining ingredients of the examples, those which are not temperature sensitive may be added at any time during the process; those ingredients which are temperature sensitive are added during the cooling process. For example, below about 110° F., DL-panthenol and phytantriol are added, and below about 100° F., the fragrances are added. Once the mixture has cooled to about 75° F., it is pumped to storage.

Later, the mixture is pumped from storage and is chilled to about 35° F. to about 48° F. The mixture is then mixed with the post-foaming agent, which itself has been prepared by blending of isobutane and isopentane.

The resulting mixture is then dispensed into an open, unpressurized container, which is capped and pressurized. I prefer to use a conventional two-chamber aerosol container in which the shaving gel is placed in one chamber, and a propellant is placed in another, separate chamber. In use, the product is dispensed from the container in gel form, and is applied to the skin to generate a foam which can be used, for example, for shaving with a razor or the like.

The same procedure used above to prepare EXAMPLES 1 through 14 may be employed to create other compositions within the scope of my invention merely by substituting alternate ingredients as desired. For example, stearic acid and palmitic acid may be omitted and a different higher fatty acid, or a different surfactant system altogether, may be substituted in their place. In like fashion, alternative post-foaming agents, or alternative optional ingredients may be employed.

Comparative Testing

A variety of tests have shown that the post-foaming shaving gel according to this invention is superior to the conventional S. C. Johnson post-foaming shaving gel discussed above. A panel of individuals found that the new post-foaming shaving gel statistically was significantly clearer than the conventional post-foaming shaving gel, had less foam as dispensed, was easier to lather, provided a moister lather, provided a lather that remained more moist, and was easier to rinse off, all at a 95% confidence level. The panel also found that the new post-foaming shaving gel was easier than the conventional post-foaming shaving gel to spread across the face, at a 90% confidence level.

In another comparative experiment, the post-foaming shaving gel according to this invention also was found to excel in a test measuring "foam speed", or the ability of the gel to retain a gel-like form. In this test, Conventional Samples 1, 2, and 3 were samples of the conventional S. C. Johnson post-foaming shaving gel, while Samples 1, 2, and 3 were samples of a post-foaming shaving gel in accordance with this invention. Sample 1 and Conventional Sample 1 each included 2.25% isopentane and 0.7% isobutane, by weight of the total post-foaming shaving gel composition; Sample 2 and Conventional Sample 2 each included 2.81% isopentane and 0.875 isobutane, by weight of the total post-foaming shaving gel composition; and Sample 3 and Conventional Sample 3 each included 3.38% isopentane and 1.05% isobutane, by weight of the total post-foaming shaving gel composition. The samples were dispensed, and the degree to which the dispensed product was gel-like was judged on a scale wherein 0 represented a gel and 10 represented a foam. Measurements were taken both initially (T=0) and five minutes later (T=5). The following results were obtained:

TABLE 5

| SAMPLE | POST-FOAMING AGENT (ISOPENTANE/ISOBUTANE) | FORM OF PRODUCT T = 0 | T = 5 |
|---|---|---|---|
| Sample 1 | 2.25/.7 | 0 | 4 |
| Conventional Sample 1 | 2.25/.7 | 0 | 8 |
| Sample 2 | 2.81/.875 | 0 | 4 |
| Conventional Sample 2 | 2.81/.875 | 5 | 10 |
| Sample 3 | 3.38/1.05 | 0 | 4 |
| Conventional Sample 3 | 3.38/1.05 | 8 | 10 |

The results in Table 5 show that the samples according to this invention (Samples 1, 2, and 3) exhibited a significantly greater ability to be dispensed in gel form, and also a significantly greater ability to retain a substantially gel form after five minutes, in comparison to the conventional S. C. Johnson post-foaming shaving gel.

Another comparative experiment, this one measuring gel strength, showed that the post-foaming shaving gel according to this invention displayed significantly improved results versus the conventional S. C. Johnson post-foaming shaving gel. The same three pairs of samples discussed above were subjected to a tine test to measure gel strength. In the tine test, a plurality of grid wires were arranged horizontally between two vertically extending, opposing side panels. The grid wires were spaced apart so that each successive pair of rods was separated by an increasingly larger distance. The post-foaming shaving gel was then dispensed across the grid wires in three ribbons perpendicular to the grid wires. Gel strength was then determined by recording how many grid wires, or "tines", on average, were spanned by the gel ribbons after a one minute wait. If a gel was strong, it would span a larger number of grid wires, while a weaker gel would not be capable of spanning grid wires having larger separations (and therefore, would fall through the gaps between those grid wires). The following results were obtained:

TABLE 6

| SAMPLE | POST-FOAMING AGENT (ISOPENTANE/ISOBUTANE) | GEL STRENGTH (TINE NUMBER) |
|---|---|---|
| Sample 1 | 2.25/.7 | 46 |
| Conventional Sample 1 | 2.25/.7 | 21 |
| Sample 2 | 2.81/.875 | 43 |
| Conventional Sample 2 | 2.81/.875 | 21 |
| Sample 3 | 3.38/1.05 | 46 |
| Conventional Sample 3 | 3.38/1.05 | 16 |

As shown by the above TABLE 6, the post-foaming shaving gel prepared in accordance with this invention provided greatly improved gel strength in comparison to the conventional S. C. Johnson post-foaming shaving gel.

In addition to displaying improved usability, the post-foaming shaving gel according to this invention also obviated the manufacturing disadvantages to which the conventional S. C. Johnson post-foaming shaving gel was subject. First, the problem of foaming during manufacturing was substantially eliminated. Secondly, after the ingredients comprising the post-foaming shaving gel according to this invention were combined, the resulting substantially liquid mixture surprisingly was transformed to a gel form at room temperature within about twenty minutes, a tremendous improvement over the two weeks and/or 130° F. temperatures required by the conventional S. C. Johnson post-foaming shaving gel. This result is especially surprising in view of the fact that the liquid mixture of this invention was found to be less, not more, viscous than the liquid mixture of the conventional S. C. Johnson post-foaming shaving gel.

INDUSTRIAL APPLICABILITY

The composition of this invention, when used as a post-foaming shaving gel may be packaged in conventional shave gel dispensers, such as, for example, aerosol cans or containers.

In addition, the composition of this invention detailed above for use in a post-foaming shaving gel, comprising (a) a surfactant system, (b) the two polymers poly(ethylene oxide) and polyvinylpyrrolidone, and (c) a post-foaming agent, may be used in many forms other than as a post-foaming shaving gel. For example, it is envisioned that the composition may instead be used in and embodied as, for example, a laundry prespotter, a drain freshener, a hard surface cleaner, or a personal cleaner such as a body wash or a hand soap, each of which preferably would be dispensed in a gel or liquid form, and then foam up upon being manually applied to a surface. For example, it is envisioned that the composition may be used in a shaving body wash comprising synthetic detergents and embodied in a liquid rather than gel form.

While this invention has been described with respect to what are at present considered to be preferred embodiments, it is to be understood that the invention is not limited to the disclosed embodiments. To the contrary, this invention is intended to cover various modifications and equivalent arrangements included within the spirit and scope of the appended claims. The following claims are to be accorded a broad interpretation, so as to encompass all such modifications and equivalent structures and functions.

What I claim is:

1. A post-foaming shaving gel composition comprising:
   about 3% to about 20% by weight of said composition of a surfactant;
   about 0.05% to about 10% by weight of said composition of poly(ethylene oxide) and polyvinylpyrrolidone, in a combined amount, wherein said poly(ethylene oxide) and said polyvinylpyrrolidone are present in a weight ratio of about 1:10 to about 10:1; and
   about 0.1% to about 10% by weight of said composition of a post-foaming agent,
   wherein said surfactant, said poly(ethylene oxide), said polyvinylpyrrolidone, and said post-foaming agent are combined together into said post-foaming shaving gel composition.

2. A composition according to claim 1, wherein said poly(ethylene oxide) and said polyvinylpyrrolidone are present in a weight ratio of about 1:1 to about 1:10.

3. A composition according to claim 2, wherein said poly(ethylene oxide) and said polyvinylpyrrolidone are present in a weight ratio of about 1:5.

4. A composition according to claim 3, wherein said poly(ethylene oxide) and said polyvinylpyrrolidone are present in a weight ratio of about 9:47.

5. A composition according to claim 1, wherein said poly(ethylene oxide) and said polyvinylpyrrolidone are present in an amount, totalled together, of about 0.6%.

6. A composition according to claim 1, wherein said poly(ethylene oxide) is a polymer having an average of about 15,000–120,000 linked ethylene oxide monomers.

7. A composition according to claim 6, wherein said poly(ethylene oxide) is a polymer having an average of about 60,000–120,000 linked ethylene oxide monomers.

8. A composition according to claim 7, wherein said poly(ethylene oxide) is a polymer having an average of about 90,000 linked ethylene oxide monomers.

9. A composition according to claim 1, wherein said polyvinylpyrrolidone has a viscosity-average molecular weight of about 630,000 Daltons.

10. A composition according to claim 9, wherein said poly(ethylene oxide) is a polymer having an average of about 90,000 linked ethylene oxide monomers.

11. A composition according to claim 2, wherein said poly(ethylene oxide) is a polymer having an average of about 60,000–120,000 linked ethylene oxide monomers.

12. A composition according to claim 1, wherein said surfactant comprises a soap.

13. A composition according to claim 12, wherein said soap comprises a water-soluble salt of a fatty acid.

14. A composition according to claim 13, wherein said fatty acid is selected from the group consisting of stearic, palmitic, myristic, oleic, coconut oil fatty acid, and mixtures thereof.

15. A composition according to claim 14, wherein said soap comprises a water-soluble salt of palmitic acid.

16. A composition according to claim 15, wherein said soap comprises a triethanolamine salt of palmitic acid.

17. A composition according to claim 14, wherein said soap comprises a water-soluble salt of stearic acid.

18. A composition according to claim 17, wherein said soap comprises a triethanolamine salt of stearic acid.

19. A composition according to claim 14, wherein said soap comprises a water-soluble salt of palmitic acid and a water-soluble salt of stearic acid.

20. A composition according to claim 19, wherein said soap comprises a triethanolamine salt of palmitic acid and a triethanolamine salt of stearic acid.

21. A composition according to claim 19, wherein said soap comprises water-soluble salts of palmitic acid and stearic acid, formed by combining a basic material with palmitic acid and stearic acid, said palmitic acid and said stearic acid being provided in a weight ratio of 1:3 to 3:1.

22. A composition according to claim 21, wherein the weight ratio of palmitic acid to stearic acid is 3:1.

23. A composition according to claim 1, wherein said surfactant is present in an amount of about 16% to 18% by weight of said composition.

24. A composition according to claim 1, wherein said surfactant comprises a soap and a synthetic detergent.

25. A composition according to claim 24, wherein said synthetic detergent is selected from the group consisting of water-soluble polyoxyethylene ethers of alkyl-substituted phenols and water-soluble polyethoxylated derivatives of fatty alcohols.

26. A composition according to claim 24, wherein said synthetic detergent is selected from the group consisting of water-soluble N-acyl sarcosine salts.

27. A composition according to claim 24, wherein said synthetic detergent is present in an amount of about 0.1% to about 8% by weight of said composition.

28. A composition according to claim 1, wherein said post-foaming agent comprises a hydrocarbon propellant.

29. A composition according to claim 28, wherein said hydrocarbon propellant is selected from the group consisting of propane, n-pentane, isopentane, neopentane, n-butane, isobutane, and mixtures thereof.

30. A composition according to claim 29, wherein said hydrocarbon propellant comprises a mixture of isobutane and isopentane.

31. A composition according to claim 30, wherein said isobutane and said isopentane are present in a weight ratio of about 1:3.

32. A composition according to claim 1, wherein said post-foaming agent is present in an amount of about 3% by weight of said composition.

33. A composition according to claim 1, further comprising water in an amount of at least about 60% by weight of said composition.

34. A composition according to claim 33, wherein said water is present in an amount of about 75% by weight of said composition.

35. A composition according to claim 1, wherein the pH of said composition is about 4 to about 10.

36. A composition according to claim 35, wherein the pH of said composition is about 7 to about 10.

37. A composition in the form of a post-foaming gel, comprising:

about 3% to about 20% by weight of said composition of a water-soluble salt of a fatty acid;

about 0.05% to about 10% by weight of said composition of (a) poly(ethylene oxide), wherein said poly(ethylene oxide) is a polymer having an average of about 60,000 to about 120,000 linked ethylene oxide monomers, and (b) polyvinylpyrrolidone, in a combined amount, wherein said poly(ethylene oxide) and said polyvinylpyrrolidone are present in a weight ratio of about 1:1 to about 1:10; and about 0.1% to about 10% by weight of said composition of a post-foaming agent comprising a hydrocarbon propellant selected from the group consisting of propane, n-pentane, isopentane, neopentane, n-butane, isobutane, and mixtures thereof, wherein said composition has a pH of about 4 to about 10, and wherein said water-soluble salt of a fatty acid, said poly(ethylene oxide), said polyvinylpyrrolidone, and said post-foaming agent are combined together into said composition in the form of a post-foaming gel.

38. A composition according to claim 37, wherein said poly(ethylene oxide) is a polymer having an average of about 90,000 linked ethylene oxide monomers.

* * * * *